United States Patent [19]

Yang et al.

[11] Patent Number: 5,374,714
[45] Date of Patent: Dec. 20, 1994

[54] PURIFIED CORIOLUS VERSICOLOR POLYPEPTIDE COMPLEX

[76] Inventors: Mable M. P. Yang; George Chen, both of Block, 17B, Fourth Floor, Baguio Villa, Hong Kong

[21] Appl. No.: 983,238

[22] Filed: Nov. 30, 1992

[51] Int. Cl.$^5$ .......................... C07K 3/00; B01D 15/08
[52] U.S. Cl. ..................... 530/350; 530/300; 530/322; 530/371; 530/395; 530/415; 530/417; 530/422; 530/823; 536/123.1; 210/656; 210/658; 210/660
[58] Field of Search ............... 530/350, 300, 322, 371, 530/395, 415, 417, 422, 823; 514/8; 536/123, 123.1; 210/658, 656, 660

[56] References Cited

U.S. PATENT DOCUMENTS

| | | | |
|---|---|---|---|
| 4,289,688 | 9/1981 | Hotta et al. | 530/395 |
| 4,820,689 | 4/1989 | Ikuzawa et al. | 514/8 |
| 5,084,160 | 1/1992 | Stewart et al. | 530/300 |

OTHER PUBLICATIONS

Yang et al, *Am. J. Chim. Med*, vol. 20, No. 3–4, pp. 221–232, 1992 (only abstract provided).
Mizuno et al, *Agric. Biol. Chem*, vol. 54, No. 11, pp. 2884–2896, 1990.
Cho et al, *Chemical Abstract*, vol. 110, p. 333, Ref. No. 228285x, 1989.

*Primary Examiner*—Michael G. Wityshyn
*Assistant Examiner*—Abdel A. Mohamed
*Attorney, Agent, or Firm*—Antonelli, Terry, Stout & Kraus

[57] ABSTRACT

A method of obtaining a novel polypeptide from a crude extraction product of polysaccharide peptide Coriolus versicolor comprising: a) boiling a water soluble powder of polysaccharide peptide Coriolus versicolor; b) centrifuging a boiled product from step a); c) filtering a centrifuged product from step b); d) purifying a solution from step c) by gel filtration chromatography; e) subjecting the purified material from step d) to HPLC using a reversed-phase at ambient temperature, wherein a solvent composition is at an acidic Ph and further includes KCl solvent, and wherein an elution system consists of a linear gradient of about 80% methanol applied at a rate of from between 0–40 minutes to obtain chromatographic peaks; f) analyzing the chromatographic peaks by monitoring for absorbance at about 230 nm, 1.0 AUFS for protein analysis and about 620 nm, 0.02 AUFS for polysaccharide analysis and collecting fractions of each peak in a microfractionator; g) filter-sterilizing each eluent of each chromatograph fraction peak, and drying product therefrom under reduced pressure; h) preparing a solution of an ampholyte mixture of the dried product and identifying structural components of the product by capillary isoelectrophoresis; and i) using gel filtration to obtain polypeptides products of from about 10K and to 50K.

9 Claims, 16 Drawing Sheets

GRAPH KEY

444 MV %
45.00 MIN.
%BG @A C/5
% C @B M/

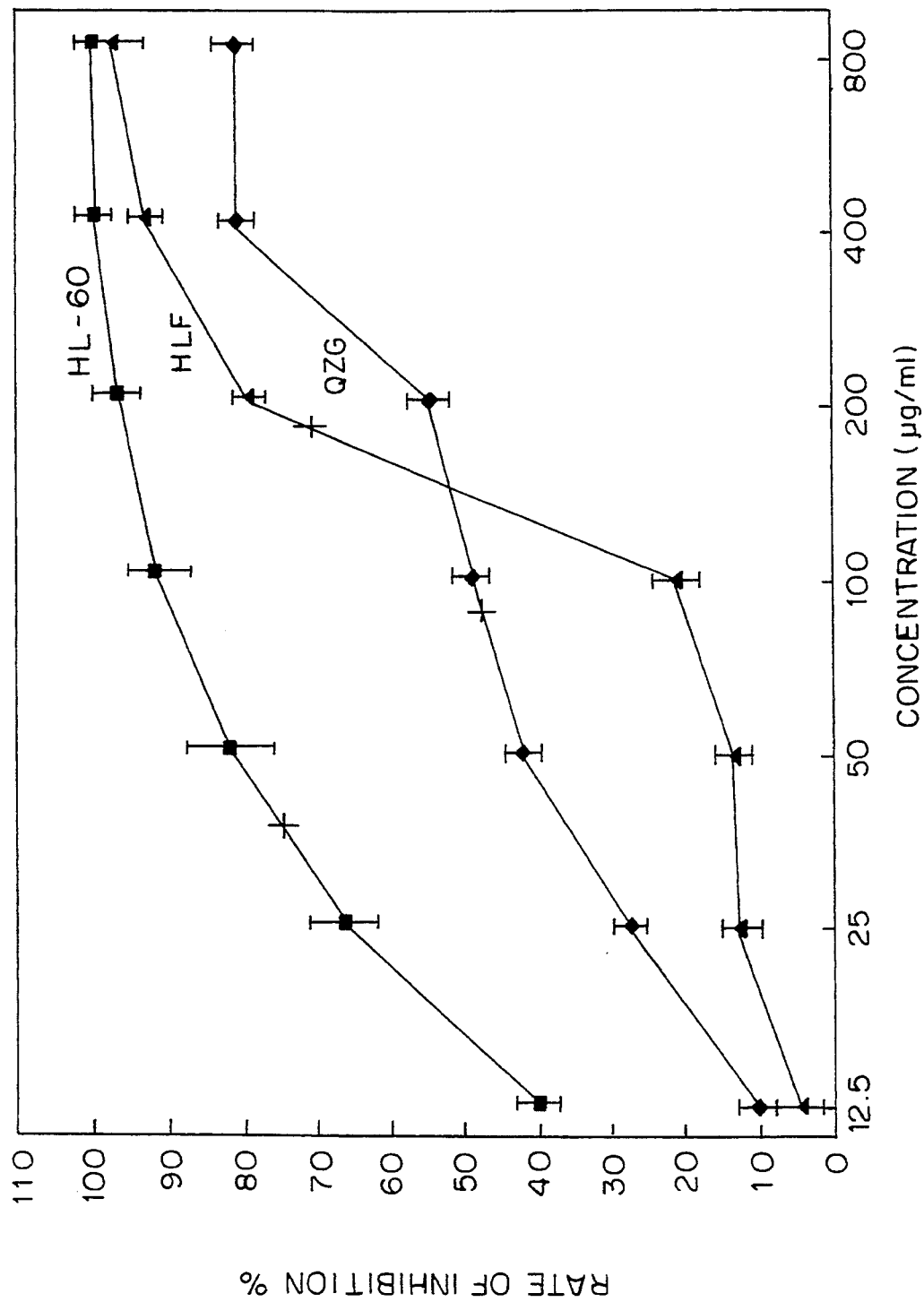

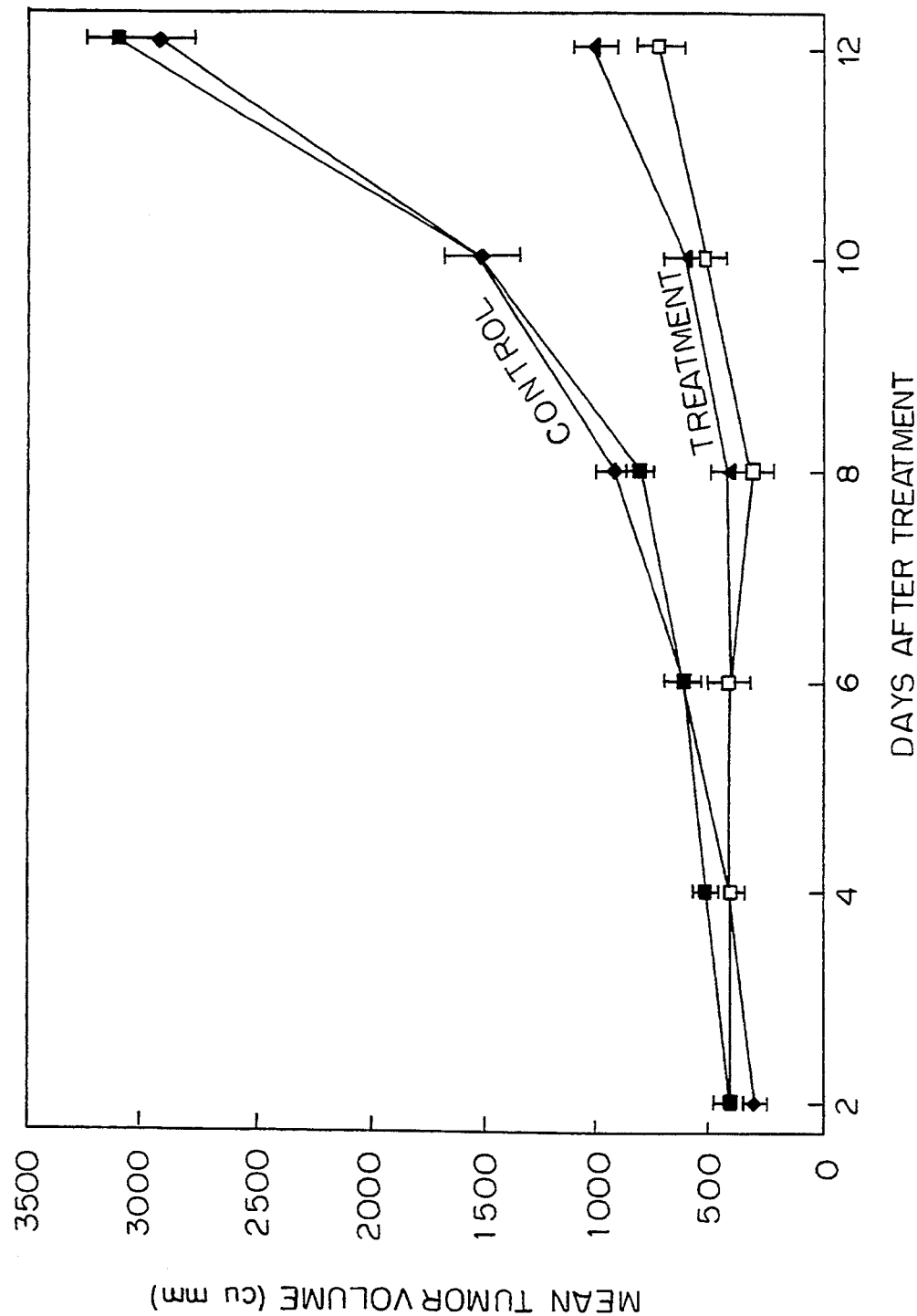

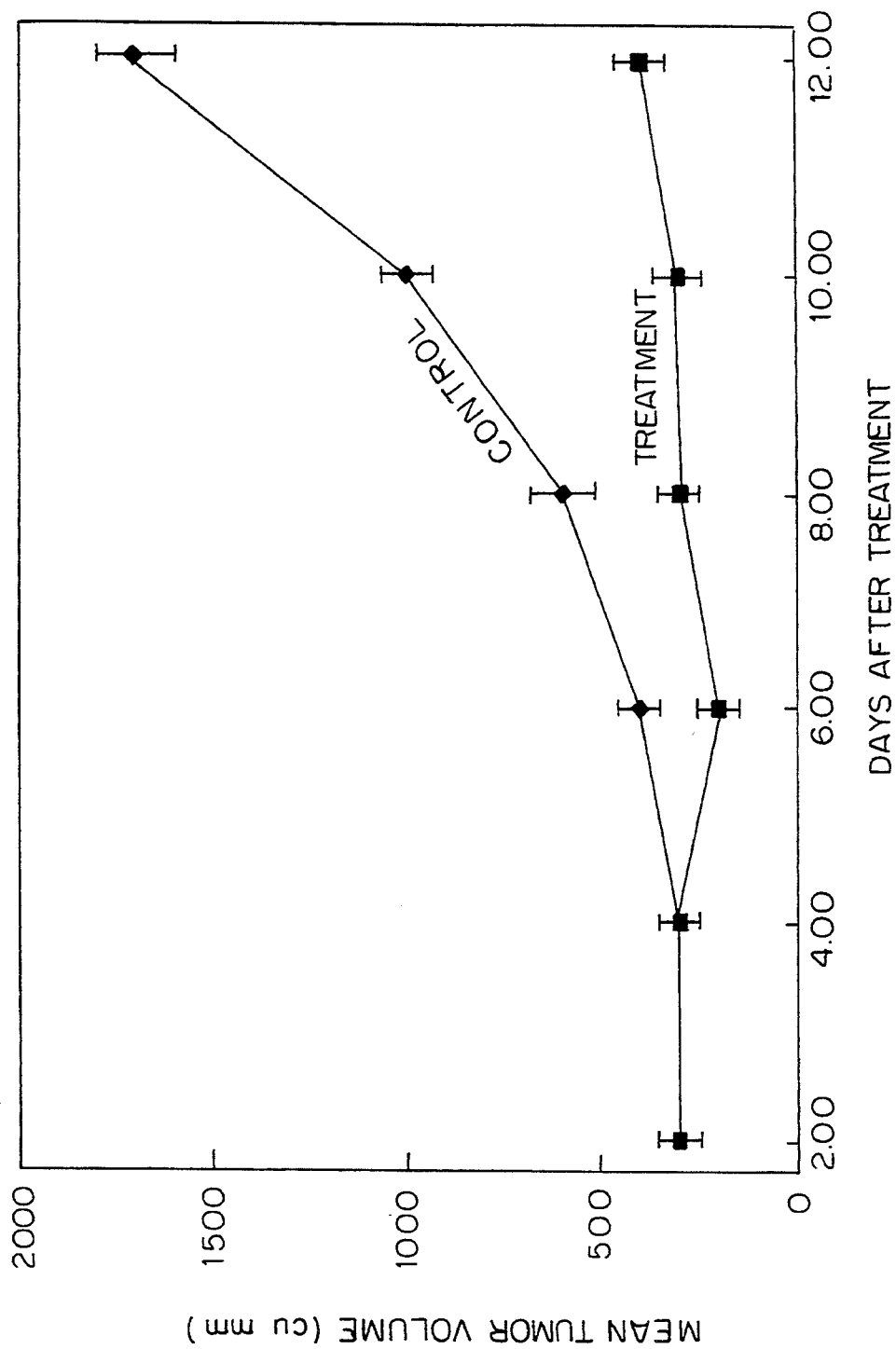

PURIFIED CORIOLUS VERSICOLOR POLYPEPTIDE COMPLEX

I. GOVERNMENT INTEREST

The invention described herein may be manufactured, used and licensed by or for the Government for governmental purposes without the payment to us of any royalties thereon.

II. FIELD OF THE INVENTION

The invention relates to obtaining purified coriolus versicolor, Cov-1 (PCV) by HPLC, after extracting the materials from first and last chromatograph peaks. The purified coriolus versicolor polypeptides from these peaks exhibit potent cytotoxic effects on human tumor cell lines but little effect on normal cell lines in vitro and inhibitory effects on the growth of tumor xenografts in Balb/c and nude mice in vivo. Further, the purified coriolus versicolor polypeptides possesses immunopotentiating effects, as they increase white blood cells while increasing the amount of T and B lymphocytes, IgG and weights of immune organs. There is no toxic effect when the purified coriolus versicolor polypeptides are administered in therapeutic doses, as shown by histo-pathological examination. The purified coriolus versicolor polypeptides have utility as anti-cancer drugs for clinical use.

III. BACKGROUND OF THE INVENTION

Historically, the mushroom has attracted considerable attention as a health-oriented food not only in China and Japan but world-wide. However, during the last decade, the anti-tumor effects of various kinds of mushroom components have been noted as a result of recent research in this field occasioned by the development of new analytical techniques to study the pharmacologically active components from mushrooms[1,2,3,4,5].

[1]. M. Torisu et al., Significant Prolongation Of Disease-Free Period Gained By Oral Polysaccharide K (PSK) Administration After Curative Surgical Operation Of Colorectal Cancer. Cancer, Imm. Imm., 32: 261–168, 1990.

[2]. J. Akiyama et al., Immunochemotherapy Of Transplanted KMT-17 Tumor In WKA Rats By Combination Of Cyclophosphamide And Immunostimulating Protein-Bound Polysaccharide Isolated From Basidiomycetes. Cancer Res. 37: 3042, 1977.

[3]. T. Mizuno et al., Antitumor Activity And Some Properties Of Water-Soluble Polysaccharides From "Ilimematsutake", The Fruiting Body Of Agaricus Blazei Murill Agric. Biol. Chem. 4: 2889–2896, 1990.

[4]. T. Mizuno et al., Antitumoractive Polysaccharides Isolated From The Fruiting Body Of Hericium Erinaceum, As Edible And Medicinal Mushroom Called Yamabushitake Or Houtouo Biosci. Biotech. Biochem., 56: 347–348, 1992.

[5]. H. Kawagishi et al., Isolation And Characterization Of A Lectin From Grifola Frondosa Fruiting Bodies. Bioch. et Biophy. Acta. 1034: 247–252, 1990.

The immunological status of a patient has been recently regarded as an important factor in the control of cancer, especially when there exists only a low tumor burden. This has given rise to the concept of the use of Biological Response Modifiers (BRM) in cancer therapy. The BRM is defined as "drugs that can regulate the relationship between the host and the tumor, leading to a biological response of therapeutic value." Therefore, there is a need extant in the area of treating patients to control cancer (especially where there exist only a low tumor burden) of finding materials capable of exhibiting immunomodulating actions as well as tumor inhibition when used clinically on various types of carcinoma.

In the area of mushrooms, the most potent strain examined was *Coriolus versicolor* in which PSK (polysaccharide Krestin) was extracted from Basidiomycetes and reported from Japan in 1965[6,7] and PSP (polysaccharide peptide) from Cov-1 (Yun Zhi) reported from China in 1984[8]. Many experimental studies and clinical investigations of PSK[1,9] and PSP[10] relate to their anti-tumor effect and especially for their potential use in cancer immunotherapy. It was found that the anti-tumor effect of PSP was more potent than that of PSK[11]. In vitro experiments of PSP were reported to inhibit the proliferation of P388 leukemia cells and Ehrlich ascites cells; it also inhibited the proliferations of some human tumor cell lines including SCG-7901, SPC, and SLY (4). In vivo experiments showed that PSP inhibited the growth of murine sarcoma 180 in tumor bearing mice[12]. The immunopotentiating effect of PSP was also noted, and it was seen that PSP increased the thymus weight and the serum C3 and IgG content of tumor bearing mice[13]. Furthermore, PSP promoted lymphocyte proliferation and increased the production of IL-2 and interferon (INF)[14]. A clinical study at the Shanghai Medical University involves 151 cases of various kinds of cancer patients who were treated with PSP, and found noticeable anti-cancer effects without toxicity to the body[10]. Since the PSP used in these studies were in crude extracts, further purifications of PSP are needed, as the mechanism of the anti-tumor effect of PSP was not clear.

[6]. Y. Nakono et al., Influence Of Protein Polysaccharide (PS-K) Isolated From Basidiomycetes On Delayed Hypersensitivity In Sarcoma-180 Bearing Mice, Proc. Japan. Cancer Assoc., 32: 282, 1973.

[7]. S Tsukagoshi et al, Kretin (PSK) Cancer Treat Rev., 11-131-155, 1984.

[8]. Q. Yang et al., Isolation Of The Polysaccharide Components Of PSP J. Shanghai Teach. Univ. (Natural Sciences Ed) 4: 36, 1986.

[9]. Y. Nio et al., In Vitro Immunomodulating Effect Of Protein Bound Polysaccharide, PSK On Peripheral Blood, Regional Nodes, And Spleen Lymphocytes In Patients With Gastric Cancer. Cancer Imm. Imm. 32: 335–341, 1991.

[10]. T. Liu et al., Clinical Implication Of PSP In Oncology In Recent Advances In Cancer, Published By Cancer Research Group, CUHK, 57–62, 1989.

[11]. X. Li et al., A Study Of Anti-Cancer Effects Of PSP And PSK On Human Tumor Cell Lines In Vitro. Acta Acad. Med., Shanghai, 14: 23–24, 1987.

[12]. J. Zhou et al., The Anti-Tumor And Immunomodulating Activity Of PSP In Mice, J. Shanghai Teach. Univ. (Natural Sciences Ed.) 3: 72, 1988.

[13]. X Li et al., "Immunomodulating Actions Of PSP, In Recent Advances In Cancer, published by Cancer Research Group, CUHK, pp. 45–56, 1989.

[14]. X Li et al, Immune Enhancement Of A Polysaccharides Peptides Isolated From Coriolus Versicolor, Acta. Pharm. Sinica, 11: 542–545, 1990.

A major object of the present invention is to provide a method for isolating polypeptides from crude PSP by high performance liquid chromatography (HPLC) and capillary isoelectrophoresis-focusing (CIEF) in order to ascertain the mechanism of the anti-tumor affect of PSP.

Another object of the present invention is to provide polypeptides of *Coriolus versicolor* that provide more potent anti-tumor affects than that of the crude extraction of PSP in which the polysaccharide peptide has a molecular weight of about 100K.

A yet further object of the present invention is to provide purified *Coriolus versicolor* polypeptides having a potent cytotoxic affects on human tumor cell lines but little affects on normal cell lines.

A further object still of the present invention is to provide purified *Coriolus versicolor* polypeptides that possess immunopotentiating affects as they increase white blood cells with increases of T and B lymphocytes, IgG and immune organs's weights, and wherein no toxic side affects are induced when these purified *Coriolus versicolor* polypeptides are administered in therapeutic doses as anti-cancer drugs for clinical use.

These and other objects of the invention will become more apparent by reference to the materials and methods hereinafter set forth.

IV. BRIEF SUMMARY OF THE INVENTION

In general, the purification method of the invention for obtaining polypeptides from crude cultured polysaccharides peptide (PSP) is obtained by extracting PSP from *Coriolus versicolor* of mycelia COV-1. A water soluble brown powder of PSP is boiled, centrifuged and filtered. Thereafter, the filtered material is purified by gel filtration chromatograph, HPLC and CIEF. Polypeptides are obtained from the purification and subsequently assayed for their anti-tumor activity, both in vivo and in vitro. The aqueous extract of PSP is purified by Sephacryl S-300 column chromatograph at a rate of 3 ml/10 min. in 10 mM sodium phosphate buffer at pH 7.2. Eluents were collected with an automatic fractionating collector, and the contents of each fraction were measured for their optical density—the wavelength corresponding to the light absorption of the peptide linkages.

Analytical HPLC was conducted using a reversed-phase column at ambient temperature, while the column was equilibrated with a buffer. Thereafter, a solvent A of $KH_2PO_4$ and the solvent B of KCL is utilized. The elution system consisted of a linear gradient of methanol applied up to a period of about 40 minutes. Analysis of chromatographic peaks were monitored by adsorbents at 230 nm, 1.0 AUFS for protein analysis and 630 nm 0.02 AUFS for polysaccharide analysis, and fractions were collected by a microfractionator. The eluent of each chromatographic fraction peak on the chromatograph were filter-sterilized and dried under reduced pressure, and the dried samples were prepared for further analysis to identify structural components and to assay their biological activities.

Capillary isoelectrophoresis focusing was then used with a solution ampholyte mixture in order to further identify the structural components of the samples. Gel filtration methods were utilized to measure the molecular weight, where a column with Sephadex G-150 was equilibrated with GBS, PBS, and ABS. The standard proteins utilized as a guide included thyroglobulin (Mr 670,000), bovine gamma globulin (Mr 158,000), chicken ovalbumin (Mr 44,000), equine myoglobin (Mr 17,000) and vitamin B 12 (Mr 1,350).

V. BRIEF DESCRIPTION OF THE DRAWINGS

The file of this patent contains at least one drawing executed in color. Copies of this patent with color drawing(s) will be provided by the Patent and Trademark Office upon request and payment of necessary fee.

FIGS. 1a and 1b are an HPLC analysis of crude PSP, wherein 2 ml of sample was injected into the HPLC system equipped with a reversed-phase column C 18 and was eluted with 10 mM $KH_2PO_4$/methanol solution;

Figure 3:
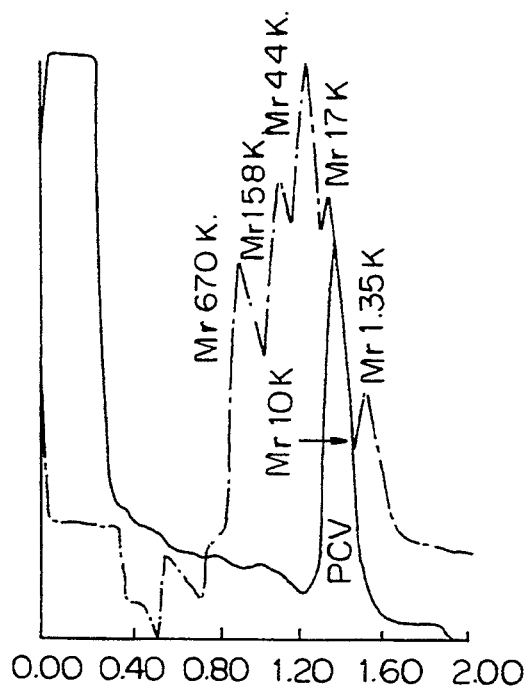

FIG. 3 shows the molecular weight of PCV (10K) was measured by using gel filtration with Sephadex G-150. This sample was compared with standard proteins. PCV Mr (10K), Thyroglobulin Mr 670K, bovine gamma globulin Mr 150K, chicken ovalbumin Mr 44K, equine myoglobin Mr 17K, vitamin B 12 Mr 1.37K.

Figure 4:
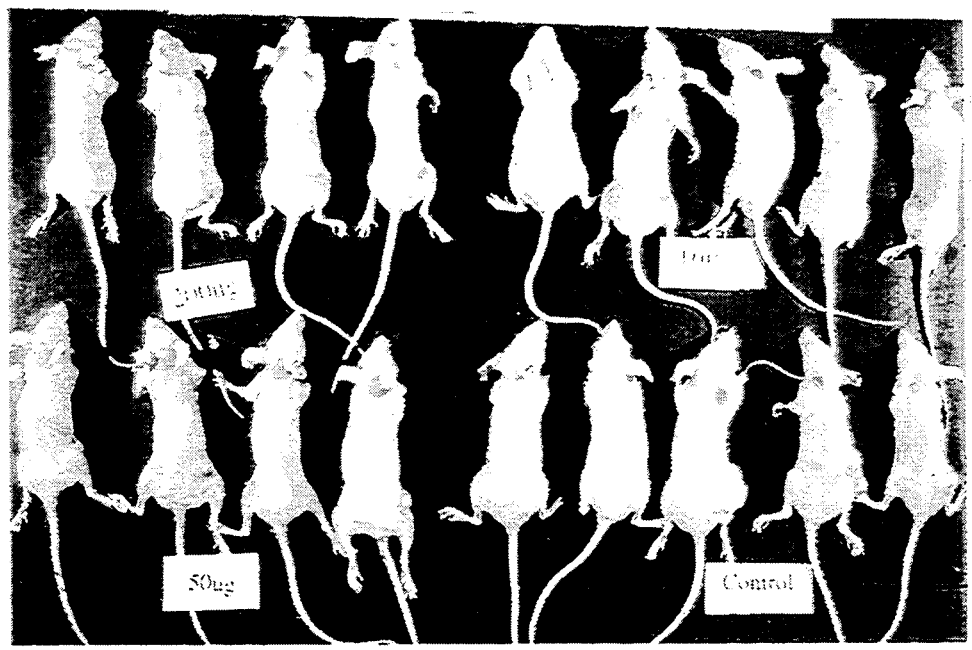

FIG. 4 is a color photograph that shows pretreatment of mice with PCV, in amounts of 2 mg×14 days, ip & iv, before inoculation of human SMMU-7721 (hepatoma cell). The incidence of tumor mass was significantly lower in PCV (10K) pretreated group. In the Control the results were: 3/5; PVC groups (50 μg/ml; $\frac{1}{4}$, 100 μg/ml; 0/5, 200 μg/ml; 0/4).

FIG. 5 shows the comparative effects of PCV (10K) on the growth of HL-60 (Leukemia cell), HLF, QZG (human normal fetal lung cells and liver cells). Cells were in the presence of the indicated drug concentration for 48 hrs. + cross indicated the growth inhibitory curve at IC 50. HL-60=30 μg/ml; HLF=180 μg/ml, QZG=90 μg/ml.

FIG. 6A shows the tumor growth curves of the Sp2/o myeloma tumor of the Balb/c mice with PCV (10K) (40 mg/kg/dose).

Figure 6B:
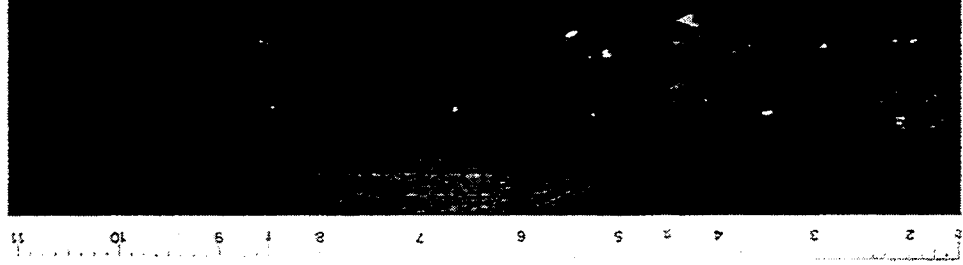

FIG. 6B is a color photograph that shows the treatment effect of PCV (10K) on tumor mass of myeloma cell (Sp2/o) in Balb/c mice. The control tumor mass is 6 times more than PCV (10K) treatment group.

FIG. 7A shows the tumor growth curves of the leukemia tumor of the nude mice with PCV (10K) (40 mg/kg/dose).

Figure 7B:
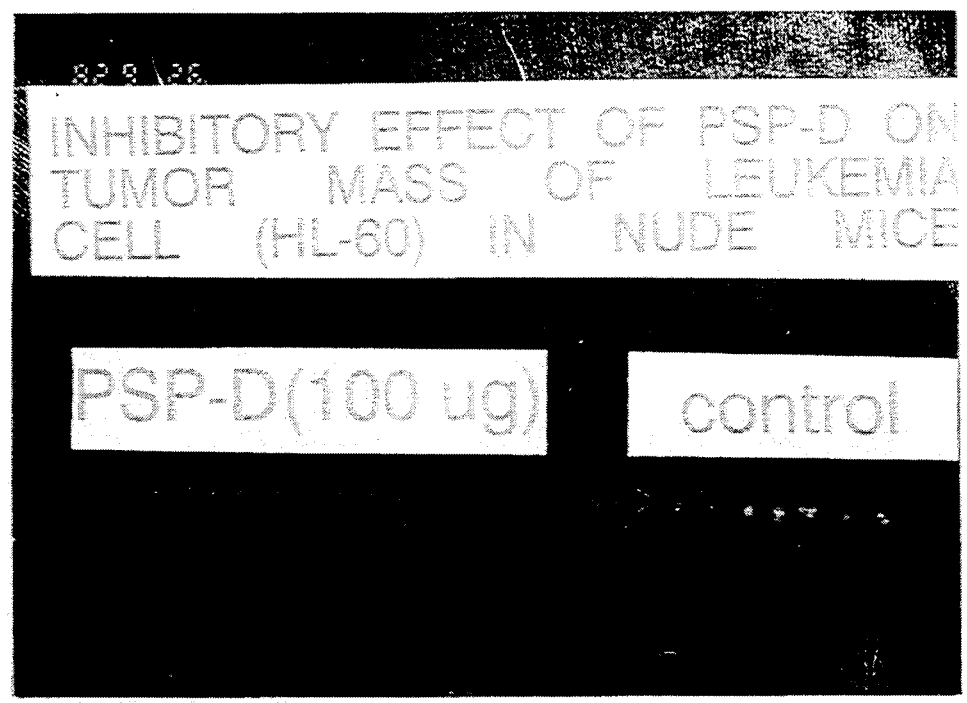

FIG. 7B shows the treatment effect of PCV (10K) on tumor mass of leukemia cell (HL-60) in nude mice. The control tumor mass is 6 times more than treatment group.

Figure 8A:
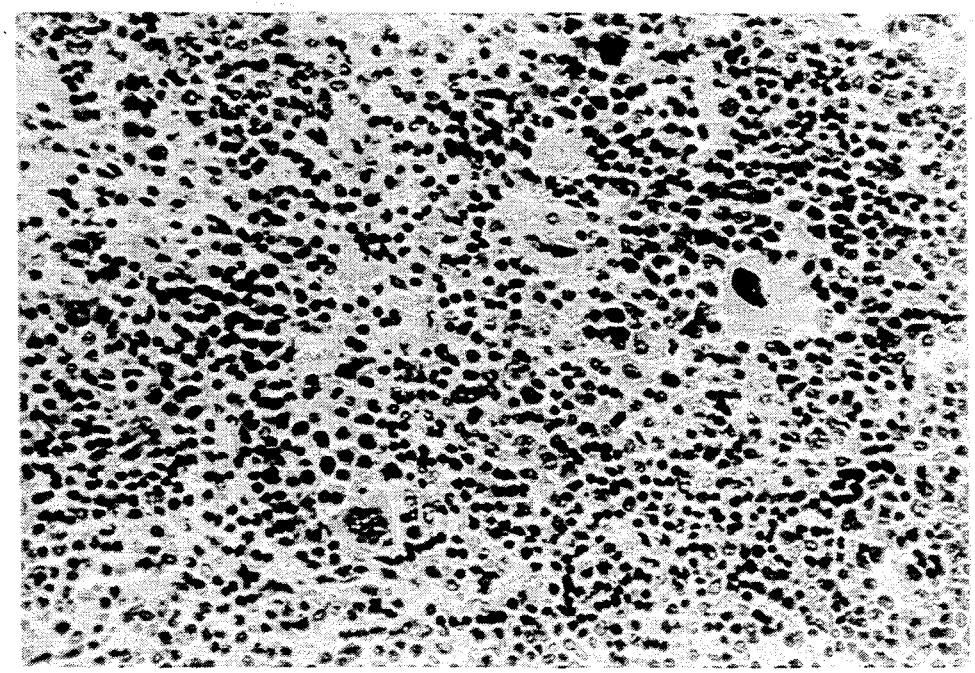

FIG. 8a is a color photograph that shows the pathological analysis (H.E. staining) of the spleen.

Figure 8B:
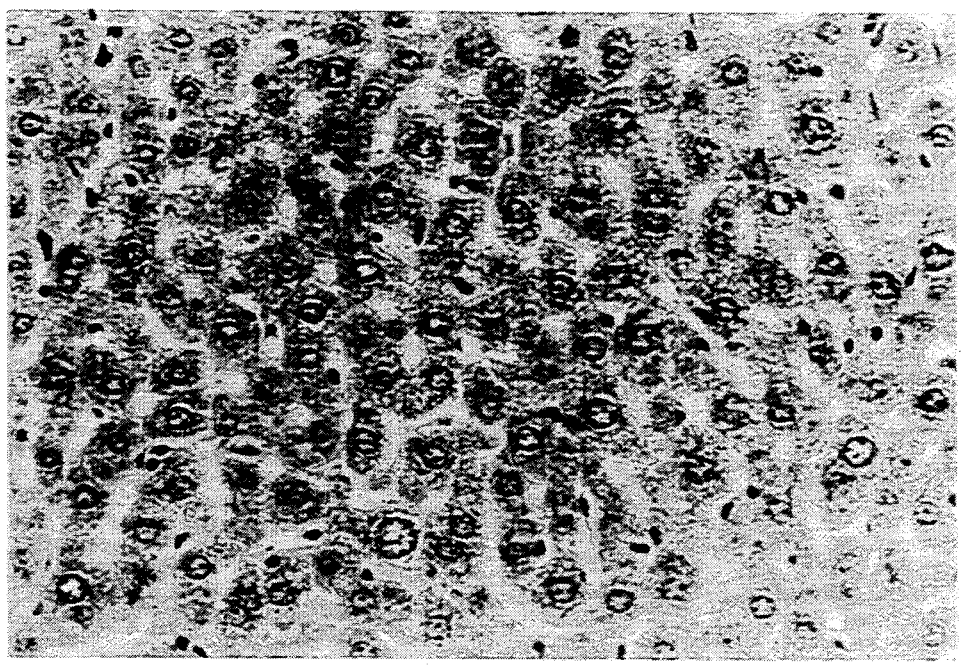

FIG. 8B is a color photograph that shoes the pathological analysis of the liver. Sections are from a mouse treated with PCV (10K) for 4 weeks, and show no pathological lesions. Some polynuclear giant cells appear in (A) at ×40.

Figure 9:
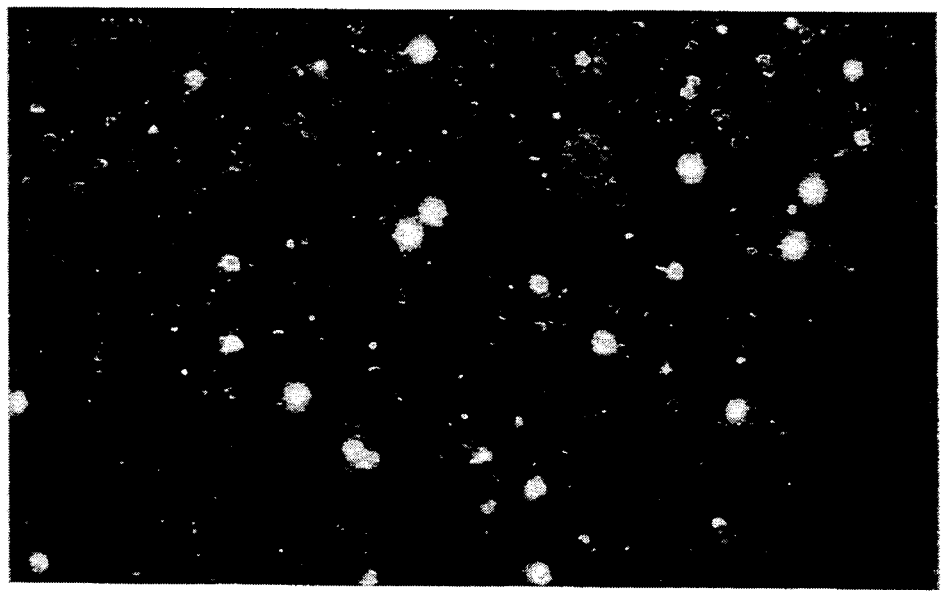

FIG. 9 is a color photograph that shows the fluorescence microscopic analysis of patient lymphocyte with PCV (10K) for 2 months. Cells were isolated from patient blood sample by facoil and than fixed on a slide at a density of $1 \times 10^6$ cells/ml. Anti-neutrophil antibody (CD15) was added to a final dilution of 1:10 for 1 h at 37° C. Then the second antibody (Rabbit anti mouse-FITC) was added for the same duration and concentration. This figure indicated immunofluorescence complex located near the cell plasma and nucleas at ×40.

Figure 10A:
Figure 10B:
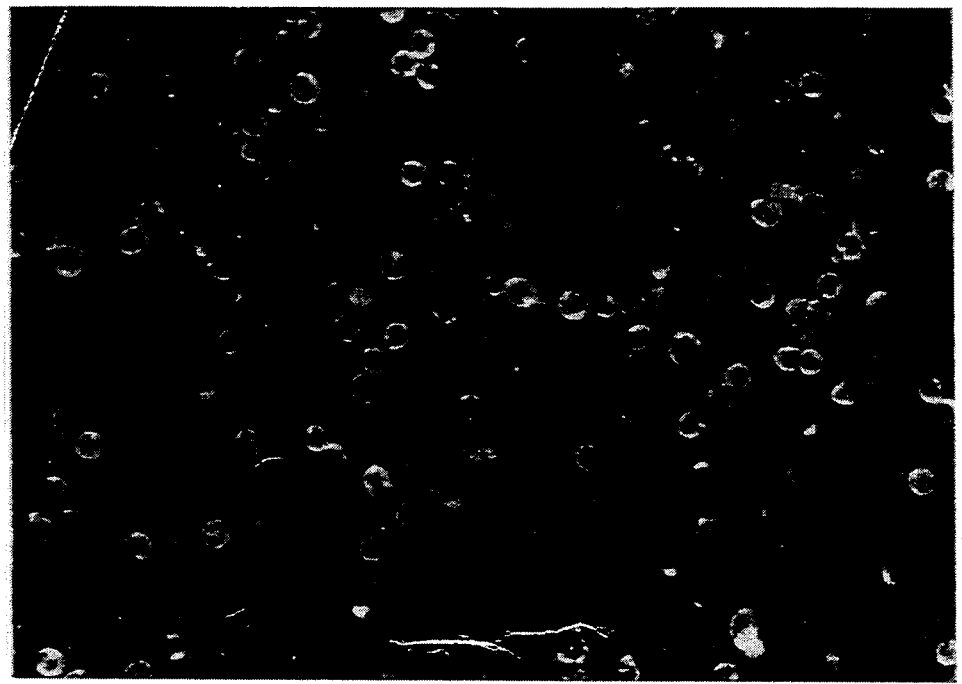

FIGS. 10A and B are color photographs that show the fluorescence microscopic analysis of mouse lymphocyte treated with PCV (10K) for 4 weeks. Cells were separated from mouse spleen organ by facoil and than attached to a slide at a density of $1 \times 10^6$ cells/ml. Anti B cell antibody (CD37) was added tot a final dilution of 20 times for 1 h at 37° C. Then the second antibody (Rabbit anti mouse-FITC) was added for the same duration and concentration. In particular, FIG. 10A is a negative control, and FIG. 10B is positive. It is shown that the immunofluorescence complex is localized mostly in the cell membrane. Some of these are distributed in the cytoplasm at ×40.

Figure 11A:
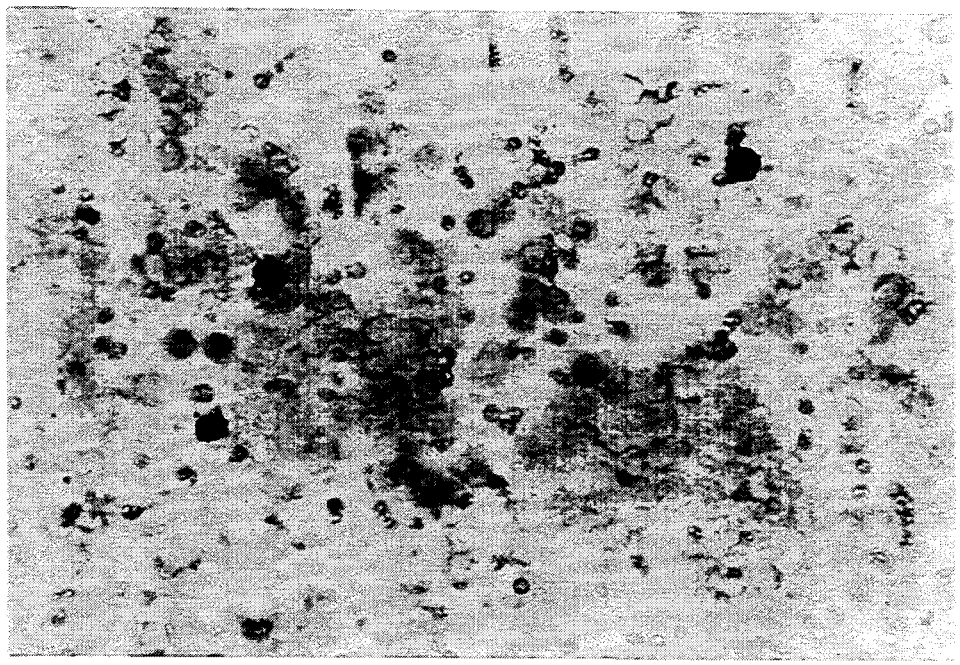
Figure 11B:
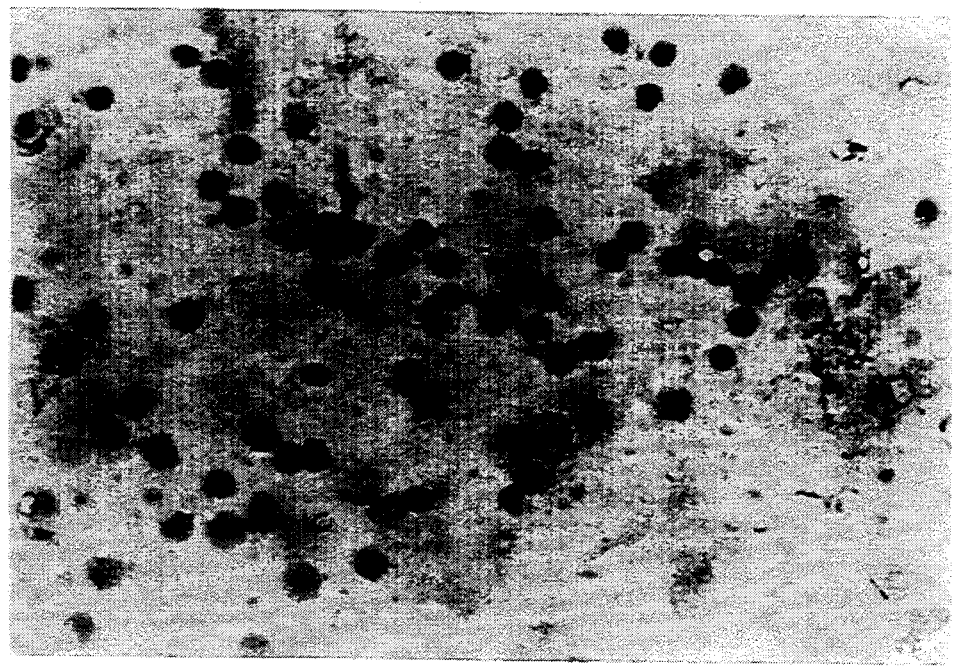

FIGS. 11A and B are color photographs that show the immunoperoxide staining analysis of patient lymphocyte with PCV (10K) for 2 months. Cells were isolated from patient blood sample by fatoil and then fixed on a slide at a density of $1 \times 10^6$ cells/ml. Anti-CD antibody were added to a final concentration of 1:20 overnight at 4° C. This was followed by incubation with a secondary biotinylated antibody (horse anti-mouse or rat) and the avidin-peroxidase complex (Vector), and followed by the addition of DAB, the final coloring agent. FIG. 11A shows CD4 immuno-complex which was located on the whole cell. FIG. 11B shows CD8 immuno-complex which was localized on the cell membrane at $\times 40$.

Figure 12A:
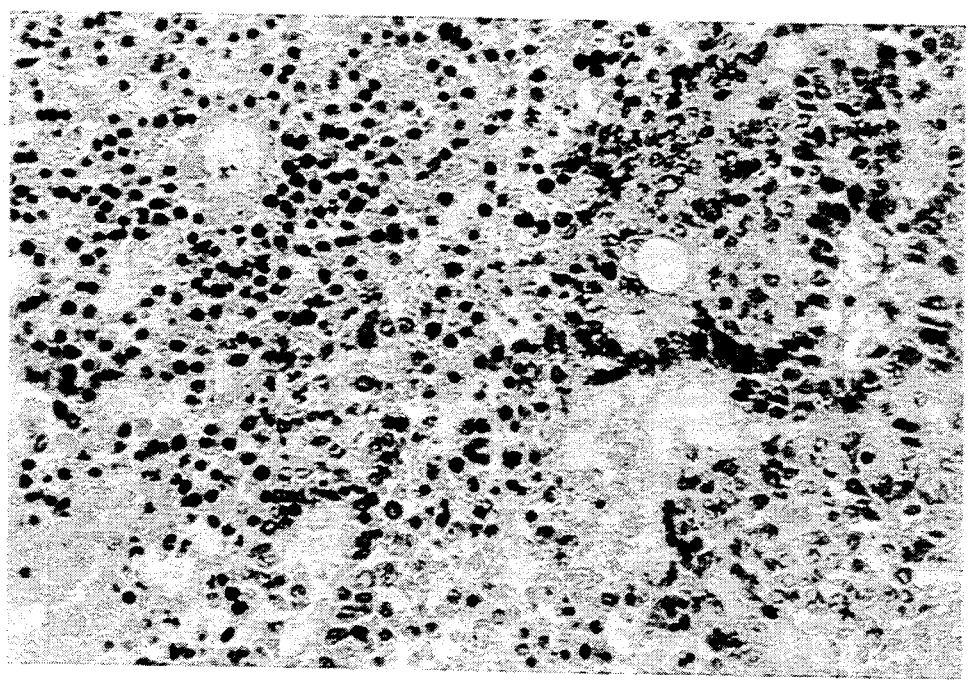
Figure 12B:
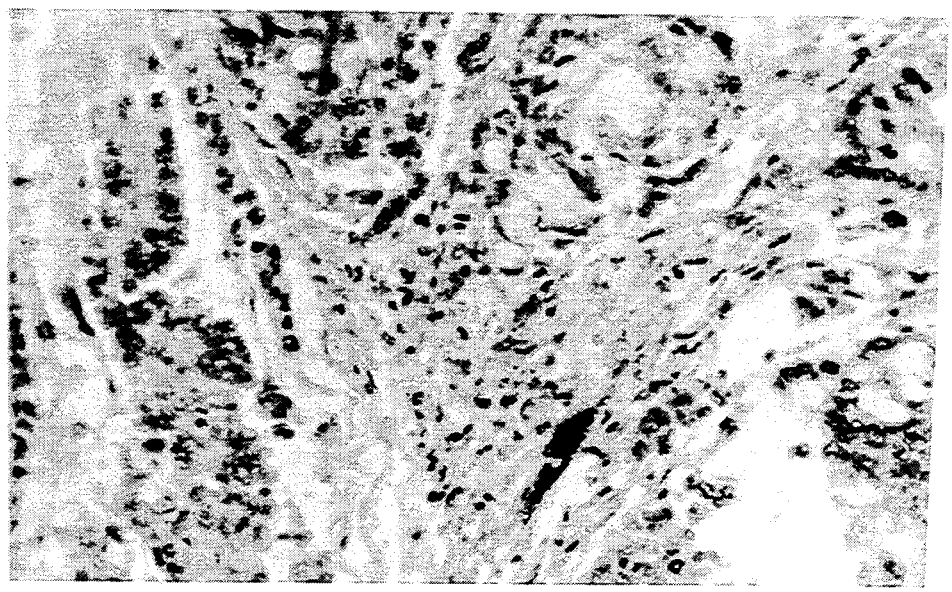

FIGS. 12A and B are color photographs that show the tumor xenografts, where some tumor cell membranes were found to be disrupted with obscure cytoplasmic structure and increased cosinophilia, representing necrotic alterations (A). In some cases, postnecrotic fibrous proliferation was encountered at the periphery of tumors (B) at $\times 40$.

Figure 13A:
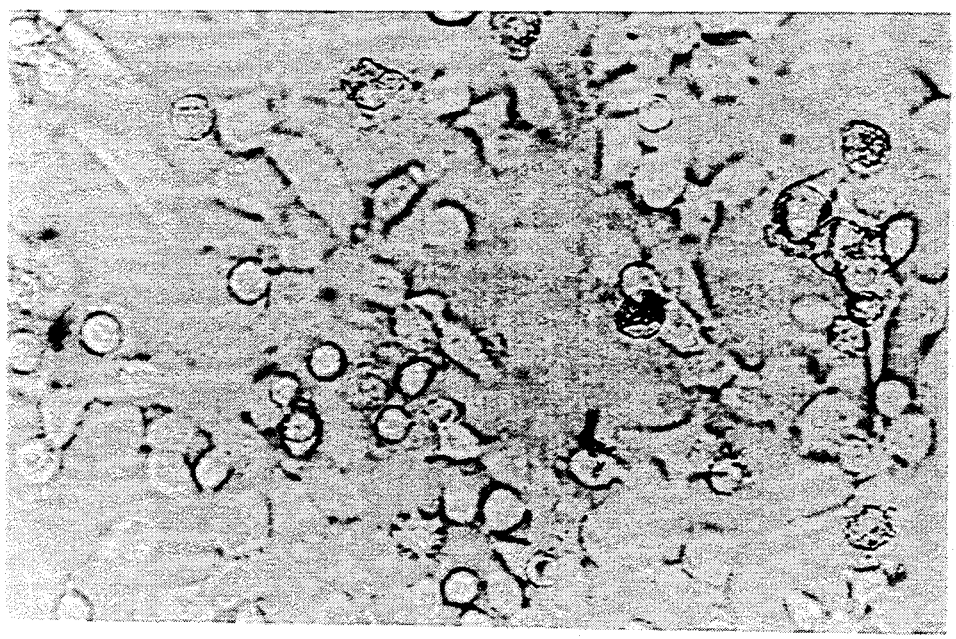
Figure 13B:
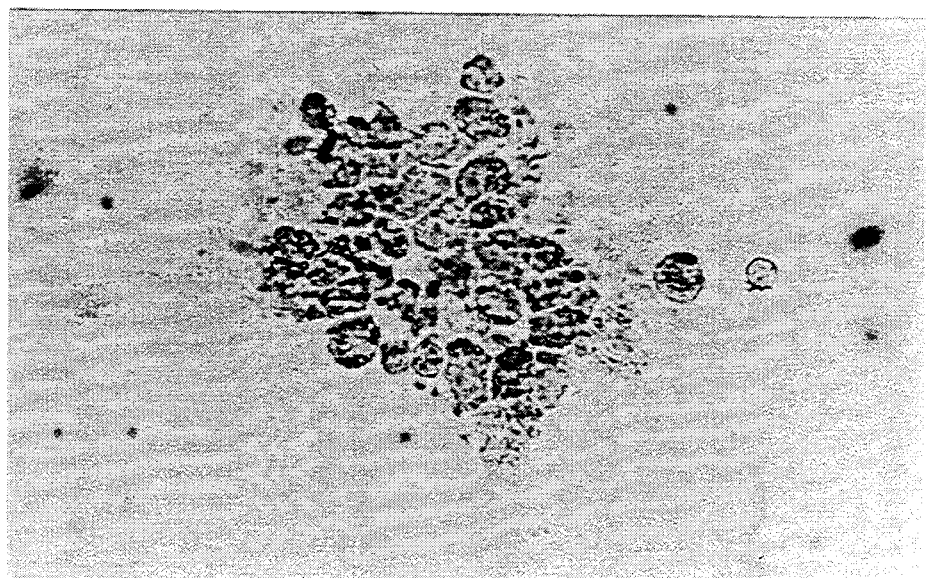

FIGS. 13A and B are color photographs that show cytotoxic effect of PCV (10K) in culture tumor cells (SCG-7901): (A) is as negative control and B was treated with PCV (10K) for 48 hrs. It is shown that the cells have been subjected to necrosis at $\times 100$.

Figure 14:
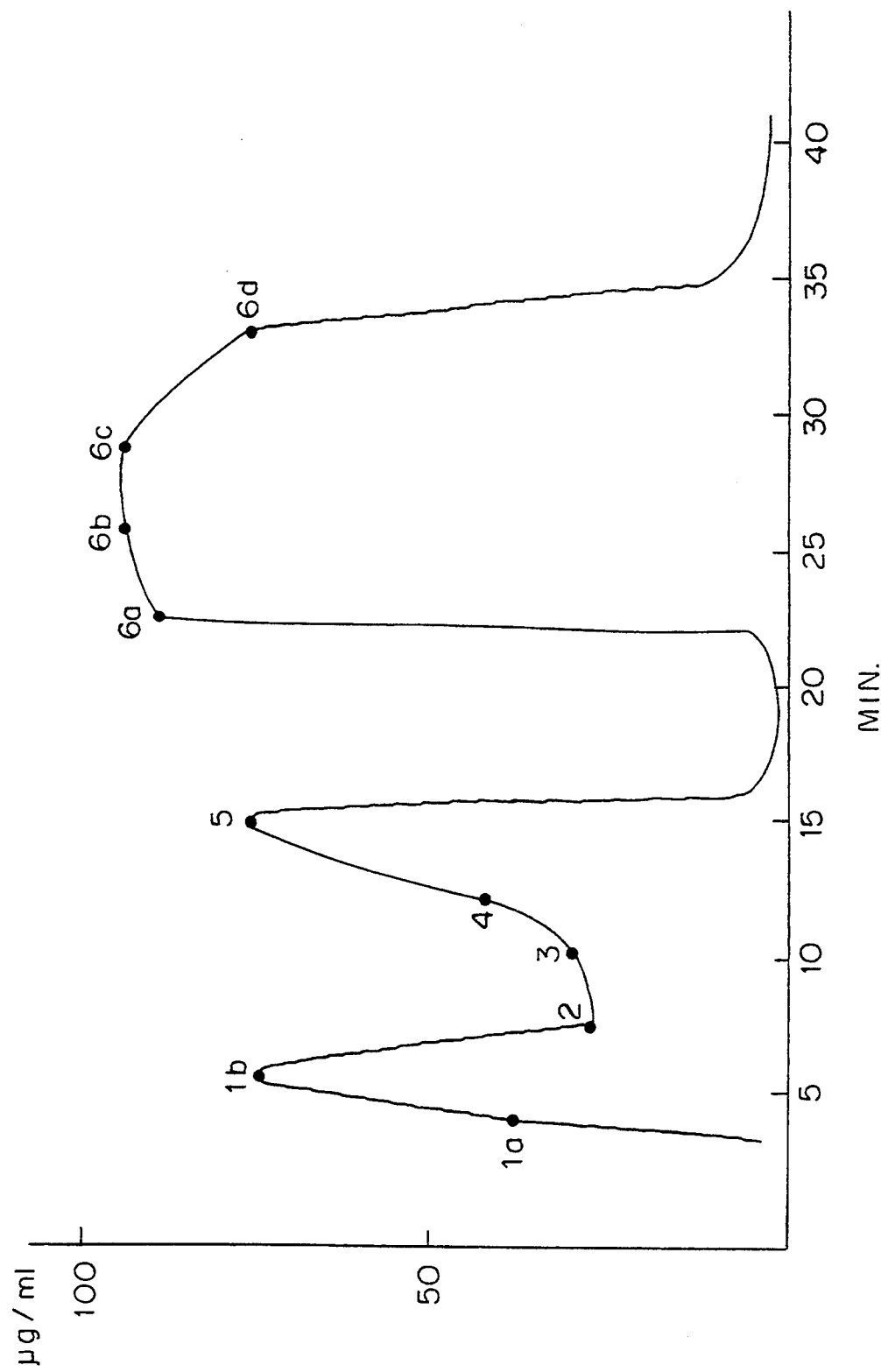

FIG. 14 shows the protein concentration in the eluent of each peak from HPLC with $KH_2PO_4$.

Figure 15:
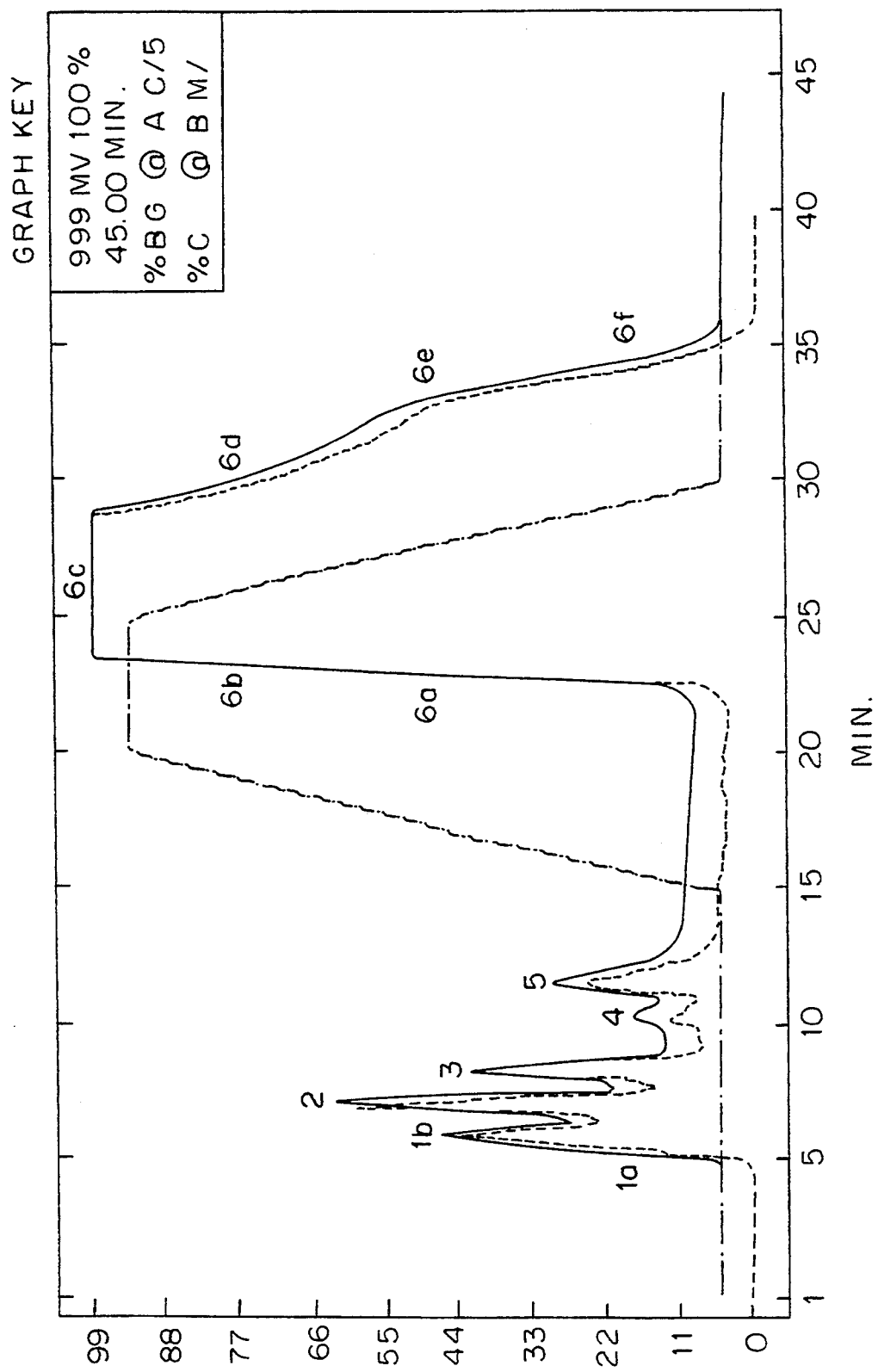

FIG. 15 shows multiple peaks of PSP sample with trifluoroacetic acid (TFA) solvent.

Figure 16:
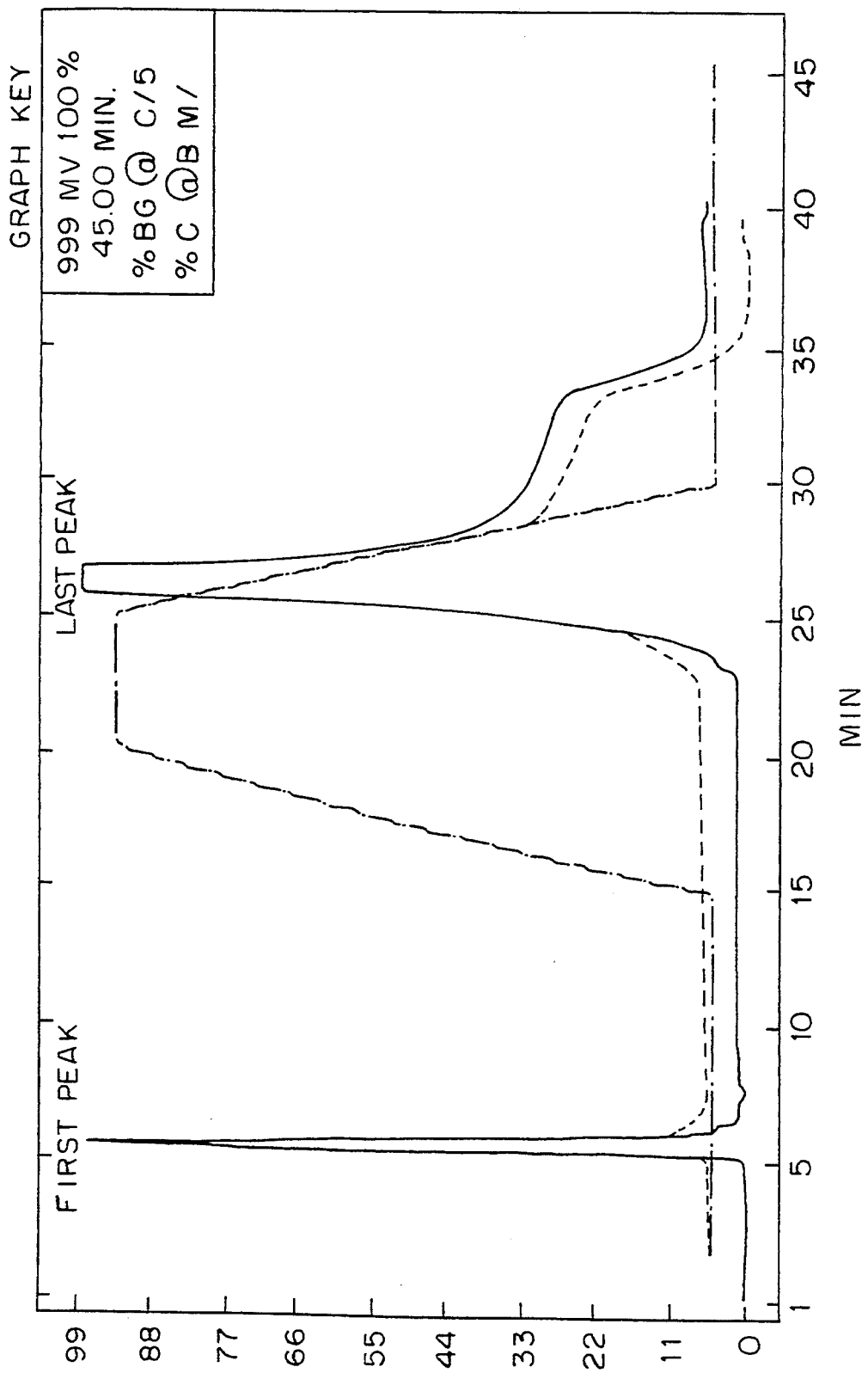

FIG. 16 shows the last peak when the PSP sample was twice subjected to HPLC using the TFA solvent.

Figure 17:
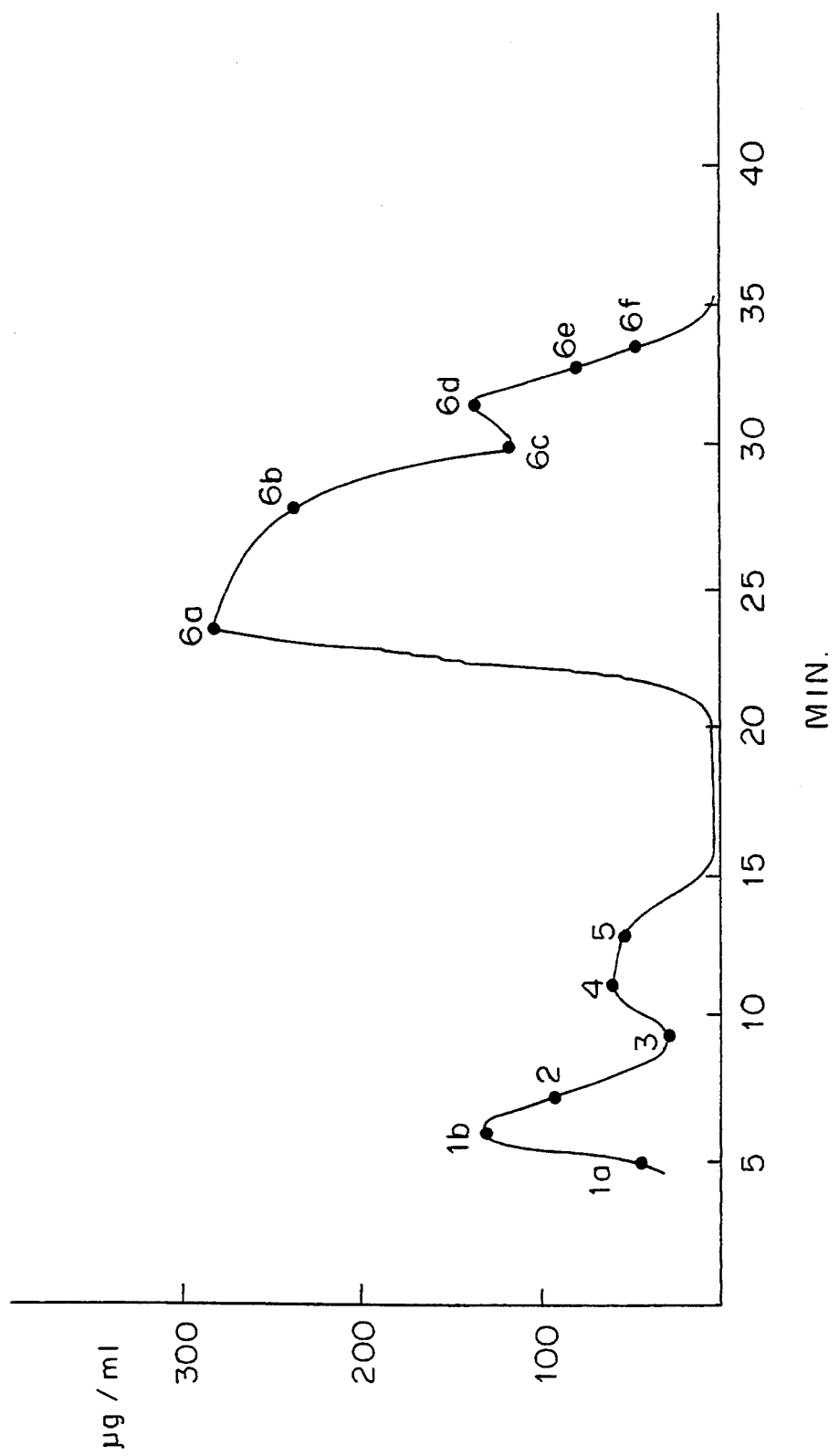

FIG. 17 shows the protein concentration in the eluent of each peak from HPLC with TFA solvent.

VI. DETAILED DESCRIPTION OF THE INVENTION

Cultured polysaccharides peptide (PSP) extracted from Coriolus Versicolor of mycelia Cov-1 was supplied by the Mushroom Research Laboratory of Shanghai Teachers University. This water soluble brown powder was boiled, centrifuged and filtered. It was purified by gel filtration chromatography, HPLC and CIEF. A small polypeptide was obtained from the above purification and assayed for its anti-tumor activity both in vivo and in vitro experiments after gel filtration column chromatography. The aqueous extract of PSP was first purified by Sephacryl S-300 column chromatograph (Pharmacia Fine Chemicals, Sweden) at a rate of 3 ml/10 min in 10 mM sodium phosphate buffer, pH 7.2. Eluents were collected with an automatic fractioning collector and the contents of each fraction were measured for their optical density at 280 nm. This wave length corresponds the light absorption of peptide linkage.

HPLC

Analytical HPLC (Bio-Rad, model 400) was conducted using a reversed-phase column (carriage of C 18 semi-preparative column) at ambient temperature. The column was equilibrated with a buffer at a flow rate of 4 ml/min. The solvent A composition was 150 mM. $KH_2PO_4$, pH 6.8 and solvent B was 200 mM KCL. The elution system consisted of a linear gradient of 80% methanol applied from 0 to 40 min. Analysis of chromatographic peaks was monitored by following absorbance at 230 nm, 1.0 AUFS for protein analysis and 620 nm 0.02 AUFS for polysaccharide analysis. Fractions were collected by a Gilson microfractionator. The eluent of each chromatograph fraction peaks on chromatograph was filter-sterilized and dried using a Speed Vac concentrator under reduced pressure. The dried samples were prepared for further analysis to identify their structure components and to assay their biological activities.

CIEF

Capillary isoelectrophoresis focusing (Bio-Rad, model 3000) was used with a solution of Ampholyte mixture to further identify the structural components of the samples. Gel filtration was used for measuring molecular weight. A column ($1.5 \times 96$ cm, Bio-Rad) with Sephadex G-150 was equilibrated with GBS, PBS, ABS. Standard proteins were from Sigma Co. (USA) and included thyroglobulin (Mr 670,000), bovine gamma globulin (Mr 158,000), chicken ovalbumin (Mr 44,000), equine myoglobin (Mr 17,000), vitamin B 12 (Mr 1,350).

IN VITRO EXPERIMENTS

A. Cultivation of Cell Lines

Cell lines obtained from standard stock culture were seeded in triplicate on microtiter cell plate dishes, test tubes or flasks and cultured for 18 hr (5% $CO_2$; 95% air at 37° C.) to allow cell growth and attachment before starting the assay. The culture medium was RPMI 1640 medium supplemented with 10% fetal calf serum, 2 ml glutamine, 50 IU/ml penicillin, 0.1 mg/ml streptomycin and 10 mM HEPES buffer (pH 7.4). Cells were subcultured once a week at a split ratio of 1:10 using trypsin-/EDTA solution and were regularly checked for mycoplasma contamination.

B. Cytotoxic Effect and Inhibition Assay on Tumor Cells

The growth of tumor cells were detected under microscope after 18 hr incubation at 37° C., in a $CO_2$ incubator. Cells ($2-4 \times 10^9$) were transferred into 55 ml flat bottom test tubes and samples of purified PSP or PCV in different concentrations were added. After incubation for 24, 48, and 72 hours the number of viable cells were determined. The influence of PSP on the inhibition of tumor cells was evaluated by measuring. $^3$H-thymidine incorporation into nuclei DNA of tumor cells. TdR was converted via the salvage pathway to thymidine triphosphate (dTTP) which is incorporated into DNA. Tumor cells which were harvested 7 days after incubation were collected by centrifugation and washed with fresh Hanks solution. Cells were then seeded in 96 well plates (Falcon), 3–5 replicate wells were used for each experimental condition. PCV (10K) samples of different concentrations were added into the wells and incubated for at least 24 hr. $^3$H-thymidine (specific activity, 1 $\mu$Ci/mM) was added to the wells and incubated with the cells for 18 hr before measurement. Cells were detached from the bottom of the test tube by shaking with a shaker. Cells were then lysed by freezing and collected by filtration on membrane filters (pore size, 0.22 $\mu$m); cells were harvested on filter membranes using an automatic cell harvester. The filters were dried and radioactivity on each filter was measured. The cellular $^3$H thymidine uptake was determined by measuring the radioactivity incorporated into DNA using a liquid scintillation fluid and a beta-scintillation counter. The inhibitory rate of incorporation of labelled precursors were calculated according to formula as follows.

$$\text{Inhibition \%} = \left(1 - \frac{\text{cpm of treated group}}{\text{cpm control group}}\right) \times 100$$

The results were also expressed as $IC_{50}$ values. The median concentration of drug required to inhibit the growth of tumor cells by 50% was determined by plotting the logarithm of the drug concentration vs the growth rate (percentage of control) of the treated cells.

IN VITRO EXPERIMENTS

A. Mice

Six-week old nude mice and Balb/C mice of both sexes, weighing 18–22 g were used as the tumor. Tumor bearing mice. Tumor cells were obtained from standard stock culture in RPMI-1640 medium, supplemented with 10% fetal calf serum, and used as inocula for in vivo growth. Tumor cells ($1 \times 10^6$) were inoculated into nude mice or Balb/c mice.

B. Experiments

The anti-tumor activities of drugs PCV or PSP were assessed in different groups of mice and are described hereafter. Anti-tumor activity was assessed in terms of tumor weight and volume. Tumor diameter was serially measured with calipers to estimate tumor size. The calculation used the following formula: Square root of long diameter×short diameter (mm). Each experimental and control group consisted of 6–10 mice. The difference in tumor growth (tumor size or tumor weight) between the control and experimental groups was tested statistically by using Student's t-test.

For evaluation of the preventive effect of the drug on tumor growth, tumor cells were inoculated at one to two weeks after drug administration. While in the study of the therapeutic effect the drug was given 10 to 15 days after inoculation of tumor cells when tumor lump sizes reached about $5 \times 5$ mm², which could be felt by finger palpation. The drugs effects were evaluated according to the percentage of tumor growth and the inhibition on the tumor growth rate. Serum IgG was measured by using a modified radial immunodiffusion method[15].

[15]. Q Yang et al, The p- io-Chemical Characteristics Of The Polysaccharide-Peptide (PSP) Of Coriolus versicolor (Yun-Zhi) In Recent Advances in Cancer, published by Cancer Research Group, CUHK, pp 7-18, 1989.

Purification of PSP and Isolation of PCV

Purification of PSP was done by using gel filtration chromatography, HPLC and CIEF. A small polypeptide was isolated from crude extraction of PSP (*Coriolus versicolor*) and thus, named PCV (polypeptide of *Coriolus versicolor*).

Figure 1A:
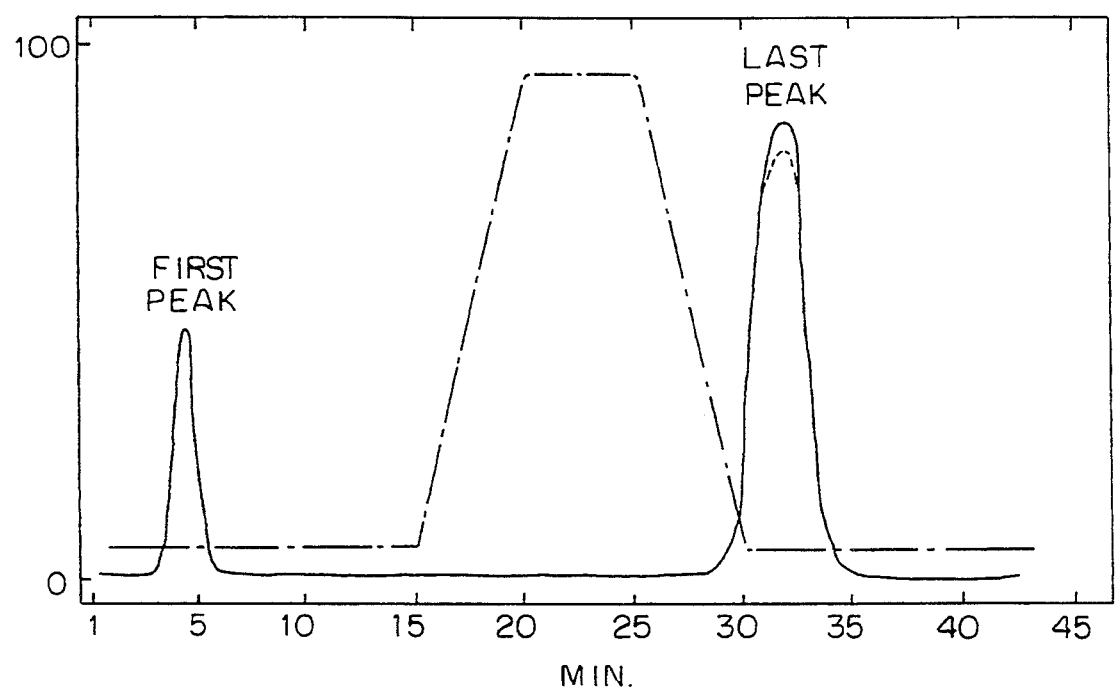
FIG. 1a shows a profile of multiple peaks from a first run of the PSP sample on HPLC.

Reference is now made to FIG. 1 which shows six peaks; however, the inhibitory effect of different fractions of PSP will show that peak numbers 1 and 6, which contain PCV polypeptides of 10K and 50K respectively are the most active in providing potent anti-tumor effects on many human tumor cell lines but little affect on normal cell lines.

TABLE 1

Inhibitory effect of different fractions of PCV (10 K) from HPLC on the growth of leukemia cells (HL-60)

| Peak No. | 1 | 2 | 3 | 4 | 5 | 6 |
|---|---|---|---|---|---|---|
| Fraction No. | 7–11 | 12–15 | 19–21 | 24–26 | 27–29 | 46–70 |
| Growth inhibition % | 90 | 71 | 53 | 53 | 49 | 64 |

PCV (10 K) was isolated from peak one (1), and PCV (50 K) was isolated from peak six (6). Incubation time 48 h. Control RPMI-1640.

Figure 1B:
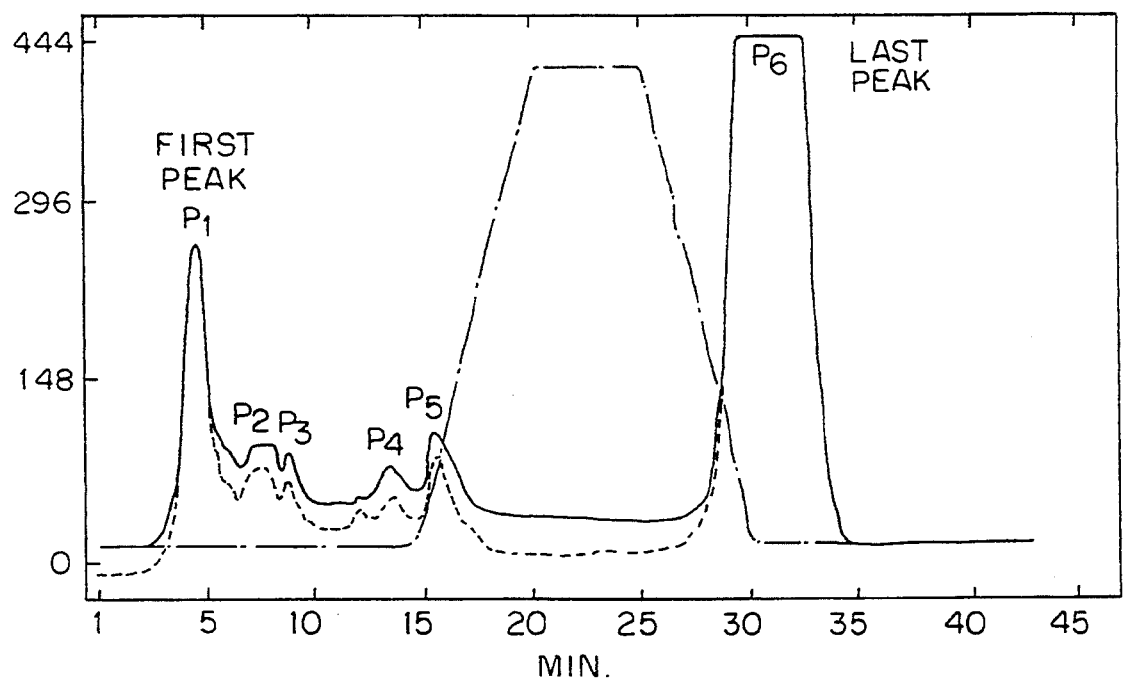
FIG. 1b shows a profile of only two peaks resulting from a second run on HPLC. The material from peaks 1 and 6 exhibit very active anti-tumor affects.
Figure 2:
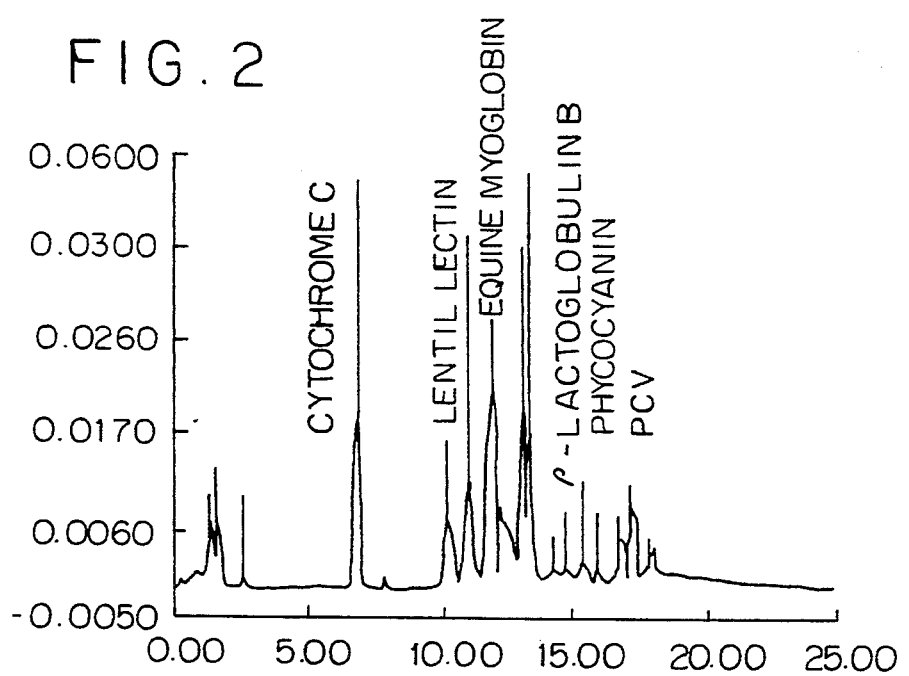
FIG. 2 shows the Capillary Isoelectrophoresis Focusing (CIEF) 17 cm×25 u coated. IEF standard proteins 50 fold dilution, ampholyte mixture detect at 200-360 nm high speed scan mode displayed on 280 nm PI value of standard proteins; cytochrome pI9.60, lentil lectin pI 7.80, β-lactoglobulin pI 5.10, phycocyanin pI 4.65, Sample of PCV pI 3-4.5.

In FIG. 1b, there are at least two significant peaks from the standpoint of the invention, and they are peaks 1 and 6, which exhibit very active inhibitory rates on the growth of leukemia cells (HL-60);

|  | Peak 1 (Falling Phase) | Peak 6 (Last) (Rising Phase) |
|---|---|---|
| Inhibitory rate on HL-60 | 50% | 60% |
| Dosage | 1 μg/ml | 1 μg/ml |

TABLE 2

Effect of PCV (10 K) on tumor metastases of nude mice implanted with human rectal carcinoma into kidney capsule

|  | Tumor weight Tumor inside Kidney capsule | Tumor metastases outside kidney |
|---|---|---|
| Saline N = 7 | 0.015 ±0.004 | 0.097 ±0.044 |
| PCV (10 K) | 0.016 ±0.007 P > 0.05 | 0.025 ±0.016 P < 0.001 |

<Tumor transplanted at two weeks after treatment>

| 0.001 |  | 0 | 2 weeks | 4 weeks |
|---|---|---|---|---|
| Neutrophil (%) | Saline (N = 4) | 1.3 +0.55 | 4.0% +0.94 | 9.0% +4.3 |
|  | PSP (N = 5) | 1.8% +0.65 | 31.4%** +0.84 | 9.6% +0.57 |
| WBC (cu mm3) | Saline (N = 4) | 6650 +536.5 | 7400 +327.4 | 7900 +1689.3 |
|  | PSP (N = 5) | 6840 +336.5 | 12910** +1413.5 | 8160 +540.5 |

*Weeks after treatment.
PSP given 2 mg/day (i.p.) × 10 days
Tumor transplanted at two weeks after treatment.

The T4, T8 numbers increased by 20% over the pretreatment.

TABLE 3

EFFECT OF PSP ON WHITE BLOOD CELLS (WBC), SERUM IgG LEVELS IN MICE

|  | CONTROl (SALINE) | PSP |
|---|---|---|
| WBC | +3100 | +7530* |
| IgG (mg/L) | +3288 | +6225* |

N = 40
*P < 0.001
PSP-S(1P): 2 mg/DAY × 10 DAYS

Comparison of the inhibitory effect on HL-60 cell between PCV (10 K), PSP & PSK

| Inhibitory rates % (X ± SD) | | | |
|---|---|---|---|
|  | 100 | 400–500 | 800–1000 |
| PCV (10 K) | 91.2 ± 2.26 | 99.3 ± 0.10 | 99.5 ± 0.10 |
| PSP | 11.7 ± 11.6 | 78.8 ± 18.0 | 87.4 ± 16.0 |
| PSK | 57.7 ± 28.9 | 33.0 ± 31.0 | 13.5 ± 18.0 |

*Dosage: μg/ml
³H TdR incorporation time: 24 hrs.
Time of drug treatment: 48 hrs.

TABLE 4

Inhibitory effect of PSP-K on [¹H] TdR incorporation (into nucleic acid) in tumor*

| PSP-K (µg/ml) | HL-60 | LS-174T | SMMU-7721 | SCG-7901 | CNE-1 2 |
|---|---|---|---|---|---|
| 50 | 81.5 ±4.79 | −9.3 ±12.4 | 31 ±3.6 | −17.9 ±49.3 | −20.3 ±16.7 |
| 100 | 91.2 ±2.26 | 18.3 ±4.9 | 44.0 ±4.4 | −13.6 ±13.2 | −65.0 ±31.0 |
| 200 | 96.4 ±1.58 | 68.5 ±4.8 | 69.7 ±7.2 | −22.4 ±46.9 | −57.0 ±23.0 |
| 400 | 99.3 ±0.10 | 89.3 ±1.5 | 77.5 ±0.7 | 64.2 ±19.0 | −34.0 ±24.0 |
| 800 | 99.5 ±0.10 | 89.3 ±1.1 | 73.0 ±2.6 | 86.0 ±4.10 | |

*[¹H] TdR incorporation time: 24 hrs.
PSP-K treatment time: 48 hrs.

TABLE 5

EFFECT OF PSP ON ORGAN WEIGHT IN MICE

| ORGAN (Mg) | CONTROL | PSP |
|---|---|---|
| LIVER | 1377.8 + 220.63 | 1658.9 + 15.94* |
| SPLEEN | 163.8 + 46.52 | 317.2 + 51.32* |
| THYMUS | 45.7 + 11.16 | 55.1 + 21.65 |
| KIDNEY** | 145.0 + 9.00 | 150.0 + 17.00 |

*$P < 0.05$;
**KIDNEY (L + R);
PSP 5 mg × 14 days, IP CONTROL (saline);
TOTAL MICE = 8

TABLE 6

EFFECT OF PSP ON TUMOR WEIGHT ON NUDE MICE IMPLANTED WITH HUMAN RECTAL CARCINOMA

| TUMOR WEIGHT (g) | TUMOR IMPLANTED (on left kidney) | TUMOR METASTASES (outside kidney) |
|---|---|---|
| Saline N = 7 | 0.015 +0.0040 | 0.097 +0.0440 |
| PSN N = 9 | 0.016 +0.0070 | 0.025 +0.0160 |
| | $P > 0.05$ | $P < 0.001$ |

TABLE 7

TREATMENT OF NUDE MICE BEARING HUMAN LEUKEMIA CELL HL-60 WITH PCV (10 K)

| GROUP (No.) | 2 | 4 | 6 | 8 | 10 | 12* |
|---|---|---|---|---|---|---|
| Treatment: | 3.29 +0.74 | 3.23 +0.54 | 2.99 +0.74 | 3.58 +0.35 | 3.90 +0.79 | 4.50 +1.06 |
| Control: | 3.27 +0.55 | 3.85 +0.57 | 4.49 +0.48 | 6.19 +1.33 | 10.64 +2.30 | 17.75 +3.25 |

8 cases/each group * Treatment days
Tumor Volume: mm³ × 100 = PCV (10 K)

TABLE 8

TREATMENT OF PVC (10 K) TO BALB/C MOUSE BEARING WITH SP2/O CELL LINE

| GROUP (No.) | 2 | 4 | 6 | 8 | 10 | 12* |
|---|---|---|---|---|---|---|
| Control: | | | | | | |
| Right | 4.74 +0.70 | 5.19 +0.61 | 6.75 +0.91 | 8.87 +0.71 | 15.61 +2.07 | 31.40 +7.19 |
| Left | 3.69 +1.18 | 4.64 +1.40 | 6.28 +1.19 | 9.80 +1.30 | 15.91 +2.52 | 29.78 +6.70 |
| Treatment: | | | | | | |
| Right | 4.37 +0.59 | 4.26 +0.83 | 4.27 +1.47 | 4.29 +1.93 | 6.02 +1.54 | 10.34 +1.78 |
| Left | +4.04 | 4.15 | 4.02 | 3.82 | 5.52** | 7.78** |
| | +0.68 | +0.81 | +1.56 | +1.45 | +1.09 | +1.30 |

Tumor volume: mm 3 × first line: right tumor mass,
Second line: left tumor mass
*Treatment days 5 cases/each group
**Left tumor mass of 2 cases have disappeared.

TABLE 9

TREATMENT OF PCV (10 K) ON ³H-TDR Incorporation IN HL-60 LEUKEMIA CELL AND QZG NORMAL LIVER CELL FETAL LUNG CELL-HLF

| PSP-D (µg/mL) | HL-60 | QZG | HLF |
|---|---|---|---|
| 12.5 | 40.1 ± 1.90 | 10.7 ± 0.04 | 4.8 ± 0.12 |
| 25 | 66.1 ± 3.27 | 27.2 ± 0.03 | 13.1 ± 0.02 |
| 50 | 81.5 ± 4.79 | 41.9 ± 0.12 | 13.6 ± 0.08 |
| 100 | 91.2 ± 2.26 | 48.4 ± 0.03 | 21.6 ± 0.02 |
| 200 | 96.4 ± 0.58 | 54.3 ± 0.15 | 79.1 ± 0.03 |
| 400 | 99.3 ± 0.10 | 80.7 ± 0.04 | 92.8 ± 0.03 |
| 800 | 99.5 ± 0.10 | 80.8 ± 0.10 | 97.1 ± 0.23 |

³H-TdR Incorporation time: 24 hrs,
PSP-D treatment time: 48 hrs.

From the foregoing data, it is apparent that cancer patients treated with purified PCV (10K or 50K) from the crude extract of *Coriolus versicolor* experience relatively low toxic side effects while benefiting therapeutically from the potent anti-tumor affects, which are superior to PSP and PSK. Further, it is apparent that, since the isolated and extracted PCV of the invention have smaller molecular weights (10K and 50K) than PSP, they are entirely different from PSP (Mr 100K) polysaccharide peptide, which has a large molecular weight, and is about from 2 to 10 times larger than the PCVs of the invention.

Moreover, the tumor inhibitory rate of PCV are much higher than those of PSP and PSK, and they inhibited the growth of human leukemia cells, colon cancer cells, hepatoma cells and stomach cancer cells, while exhibiting less cytotoxicity to human normal cells, inclusive of normal liver cells.

It should be noted that, when trifluoroacetic acid (TFA) is used in lieu of $KH_2PO_4$ as the solvent in the HPLC process, the protein content is much higher, and this is borne out by comparing the results in FIGS. 14-17. In the TFA solvent group, the second peak is also in the first peak of the $KH_2PO_4$ solvent group. In other words, the HPLC method of the invention may be accomplished with two different solvents; namely, $KH_2PO_4$ and TFA, and the smaller proteins useful within the context of the invention will be obtained from the first peak of the $KH_2PO_4$ solvent group and the first and second peaks of the TFA solvent group, while the larger proteins will be obtained from the last peaks of the $KH_2PO_4$ and TFA solvent groups.

The PCVs of the invention also possess immunopotentiating affects as they increased white blood cell counts and serum IgG levels. They also increased the organ weight of the liver, spleen and thymus.

Therefore, since the ideal anti-cancer drug is one that directly destroys cancer cells and indirectly stimulates the body's immune system activity while having less toxic side affects on the body, it is apparent that the PCVs of the invention are characterized by all of the desired characteristics for an anti-cancer drug.

What is claimed is:

1. A method of obtaining novel polypeptide products from a crude extraction product of polysaccharide-peptide Coriolus versicolor or mycelia COV-1 comprising:
   a) boiling an aqueous solution of a water soluble powder of polysaccharide peptide Coriolus versicolor of mycelia COV-1;
   b) centrifuging the boiled product from step a);
   c) filtering the centrifuged product from step b);
   d) purifying the filtered solution from step c) by gel filtration chromatography;
   e) subjecting the purified material from step d) to high performance liquid chromatography (HPLC) using a reversed-phase column at ambient temperature, wherein the solvent composition for said HPLC is at an acidic pH and includes KCl solvent, and wherein the elution system for said HPLC consists of a linear gradient of about 80% methanol applied at a rate of from about 0 to 40 minutes to obtain chromatographic peaks;
   f) analyzing said chromatographic peaks by monitoring for absorbance at about 230 nm, 1.0 absorbance unit full scale for protein analysis and about 620 nm, 0.02 absorbance unit full scale for polysaccharide analysis and collecting fractions corresponding each peak in a microfractionator;
   g) filter-sterilizing each eluent of each said fraction, and drying the product therefrom under reduced pressure;
   h) preparing a solution of an ampholyte mixture of said dried product and identifying structural components of the product in solution by capillary isoelectrophoresis; and
   i) using gel filtration to obtain polypeptide products having molecular weights of from about 10K to about 50K.

2. The process of claim 1, wherein said solvent composition further includes $KH_2PO_4$ or trifluoroacetic acid.

3. The process of claim 2, wherein said solvent composition includes $KH_2PO_4$.

4. The process of claim 2, wherein said solvent composition includes trifluoroacetic acid.

5. The process of claim 3, wherein the high performance liquid chromatography is conducted using a cartridge of C 18 semi-preparative column equilibrated with a buffer at a flow rate of about 4 ml/min., said acidic pH is 6.8 and the KCl solvent is present at 200 mM.

6. A polypeptide product having a molecular weight of about 10K obtained by the process of claim 5.

7. A polypeptide product having a molecular weight of about 50K obtained by the process of claim 5.

8. A polypeptide product having a molecular weight of about 10K obtained by the process of claim 4.

9. A polypeptide product having a molecular weight of about 50K obtained by the process of claim 4.

* * * * *